US008669523B2

(12) United States Patent
Chen et al.

(10) Patent No.: US 8,669,523 B2
(45) Date of Patent: Mar. 11, 2014

(54) CONTOUR-BASED DEFECT DETECTION USING AN INSPECTION APPARATUS

(75) Inventors: Chien-Huei Chen, San Jose, CA (US); Peter White, San Francisco, CA (US); Michael J. Van Riet, Sunnyvale, CA (US); Sankar Venkataraman, San Jose, CA (US); Hai Jiang, Panorama City, CA (US); Hedong Yang, Santa Clara, CA (US); Ajay Gupta, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/410,506

(22) Filed: Mar. 2, 2012

(65) Prior Publication Data

US 2012/0298862 A1 Nov. 29, 2012

Related U.S. Application Data

(60) Provisional application No. 61/489,871, filed on May 25, 2011.

(51) Int. Cl.
*H01J 37/28* (2006.01)
*G01N 23/04* (2006.01)
*G06T 5/50* (2006.01)

(52) U.S. Cl.
CPC . *H01J 37/28* (2013.01); *G06T 5/50* (2013.01); *G01N 23/04* (2013.01)
USPC .............................. 250/306; 250/307; 250/310

(58) Field of Classification Search
CPC ................ H01J 37/28; H01J 2237/221; G06T 2207/30148; G06T 2207/10061; G06T 5/50; G06T 7/001; G01N 21/95607; G01N 21/956; G01N 23/04; G06K 9/49; G06K 9/6206
USPC .......................... 250/306, 607, 610, 307, 310
See application file for complete search history.

(56) References Cited

U.S. PATENT DOCUMENTS

| | | | | |
|---|---|---|---|---|
| 6,661,515 | B2 * | 12/2003 | Worster et al. | 356/394 |
| 7,126,699 | B1 * | 10/2006 | Wihl et al. | 356/625 |
| 7,154,605 | B2 * | 12/2006 | Worster et al. | 356/435 |
| 7,329,868 | B2 * | 2/2008 | Takane et al. | 250/310 |
| 7,346,883 | B2 * | 3/2008 | Keck et al. | 700/121 |
| 7,904,845 | B2 * | 3/2011 | Fouquet et al. | 716/136 |
| 7,975,245 | B2 * | 7/2011 | Florence et al. | 716/52 |
| 8,124,303 | B2 * | 2/2012 | Hiroshima | 430/5 |
| 8,139,843 | B2 * | 3/2012 | Kulkarni et al. | 382/144 |
| 8,331,637 | B2 * | 12/2012 | Bar-Aviv et al. | 382/128 |

(Continued)

OTHER PUBLICATIONS

PCT International Search Report and Written Opinion of the International Searching Authority for International Application No. PCT/US2012/032796, Jan. 10, 2013, 9 sheets.

*Primary Examiner* — David A Vanore
(74) *Attorney, Agent, or Firm* — Okamoto & Benedicto LLP (57) ABSTRACT

One embodiment relates to a method of inspecting a site location on a target substrate. Contours are obtained, the contours having been generated from a reference image using a design clip. A target image of the site location is acquired. The contours are aligned to the target image, and contrast values are computed for pixels on the contours. A threshold is applied to the contrast values to determine contour-based defect blobs. Another embodiment relates to a method of generating contours for use in inspecting a site location for defects. Other embodiments, aspects and features are also disclosed.

10 Claims, 7 Drawing Sheets

(56) References Cited

U.S. PATENT DOCUMENTS

| | | |
|---|---|---|
| 8,384,903 B2 * | 2/2013 | Nielsen et al. .............. 356/445 |
| 2008/0130982 A1 | 6/2008 | Kitamura et al. |
| 2008/0277591 A1 * | 11/2008 | Shahar et al. .............. 250/394 |
| 2009/0007052 A1 | 1/2009 | Yang et al. |
| 2009/0028403 A1 * | 1/2009 | Bar-Aviv et al. .............. 382/128 |
| 2009/0052765 A1 | 2/2009 | Toyoda et al. |
| 2010/0310180 A1 | 12/2010 | Toyoda et al. |
| 2011/0276935 A1 * | 11/2011 | Fouquet et al. .............. 716/112 |
| 2011/0286656 A1 * | 11/2011 | Kulkarni et al. .............. 382/144 |
| 2012/0058421 A1 * | 3/2012 | Hiroshima .............. 430/5 |
| 2012/0298862 A1 * | 11/2012 | Chen et al. .............. 250/307 |

* cited by examiner

CONTOUR-BASED DEFECT DETECTION USING AN INSPECTION APPARATUS

CROSS-REFERENCE TO RELATED APPLICATION(S)

The present application claims the benefit of U.S. provisional patent application No. 61/489,871, filed May 25, 2011, the disclosure of which is hereby incorporated by reference in its entirety.

BACKGROUND OF THE INVENTION

1. Field of the Invention

The present invention relates to inspection and review of substrates, such as, for example, semiconductor wafers and reticles for lithography.

2. Description of the Background Art

In a conventional electron beam (e-beam) inspection instrument, a manufactured substrate (such as a silicon wafer or a reticle) is scanned with a focused beam of electrons which results in the emission of secondary electrons from the substrate surface. The emitted electrons are detected, and the detection data is typically converted into images of the surface of the specimen. These images are then analyzed numerically to detect abnormalities (referred to as defects) in the manufactured substrate. The detected defects may be subsequently reviewed by further imaging.

The detected defects may also be classified, either manually or automatically, into different classes or categories. The classification of a defect may be used to determine its cause such that appropriate adjustments may be made in the manufacturing process so as to improve its yield.

It is highly desirable to improve methods and apparatus for the detection and classification of defects imaged by electron beam instrumentation.

SUMMARY

One embodiment relates to a method of inspecting a site location on a target substrate. Contours are obtained, the contours having been generated from a reference image using a design clip. A target image of the site location is acquired. The contours are aligned to the target image, and contrast values are computed for pixels on the contours. A threshold is applied to the contrast values to determine contour-based defect blobs.

Another embodiment relates to an apparatus to detect defects in a manufactured substrate. The apparatus includes at least a source, a scanning system, a detection system, and a control and processing system. The source is configured for generating an incident electron beam. The scanning system is configured to controllably deflect the incident electron beam such that the incident electron beam is scanned over a target region such that secondary electrons are emitted therefrom. The detection system is configured for detection of the secondary electrons so as to generate an image data frame of the target region. The control and processing system is configured to obtain contours which are generated from a reference image using a design clip, acquire a target image of the site location, align the contours to the target image, compute contrast values for pixels on the contours; and apply a threshold to the contrast values to determine contour-based defect blobs.

Another embodiment relates to a method of generating contours for use in inspecting a site location for defects. A reference image is acquired of a reference site that corresponds to the site location. A design clip of the site location is retrieved. The design clip is aligned to the reference image. The contours are extracted from the reference image using the design clip.

Other embodiments, aspects and features are also disclosed.

DETAILED DESCRIPTION

Methods and apparatus for contour-based defect detection and classification using an e-beam apparatus are disclosed herein. These methods and apparatus may be employed to substantially improve the sensitivity of defect detection when compared against a conventional die-to-die approach.

Figure 1:
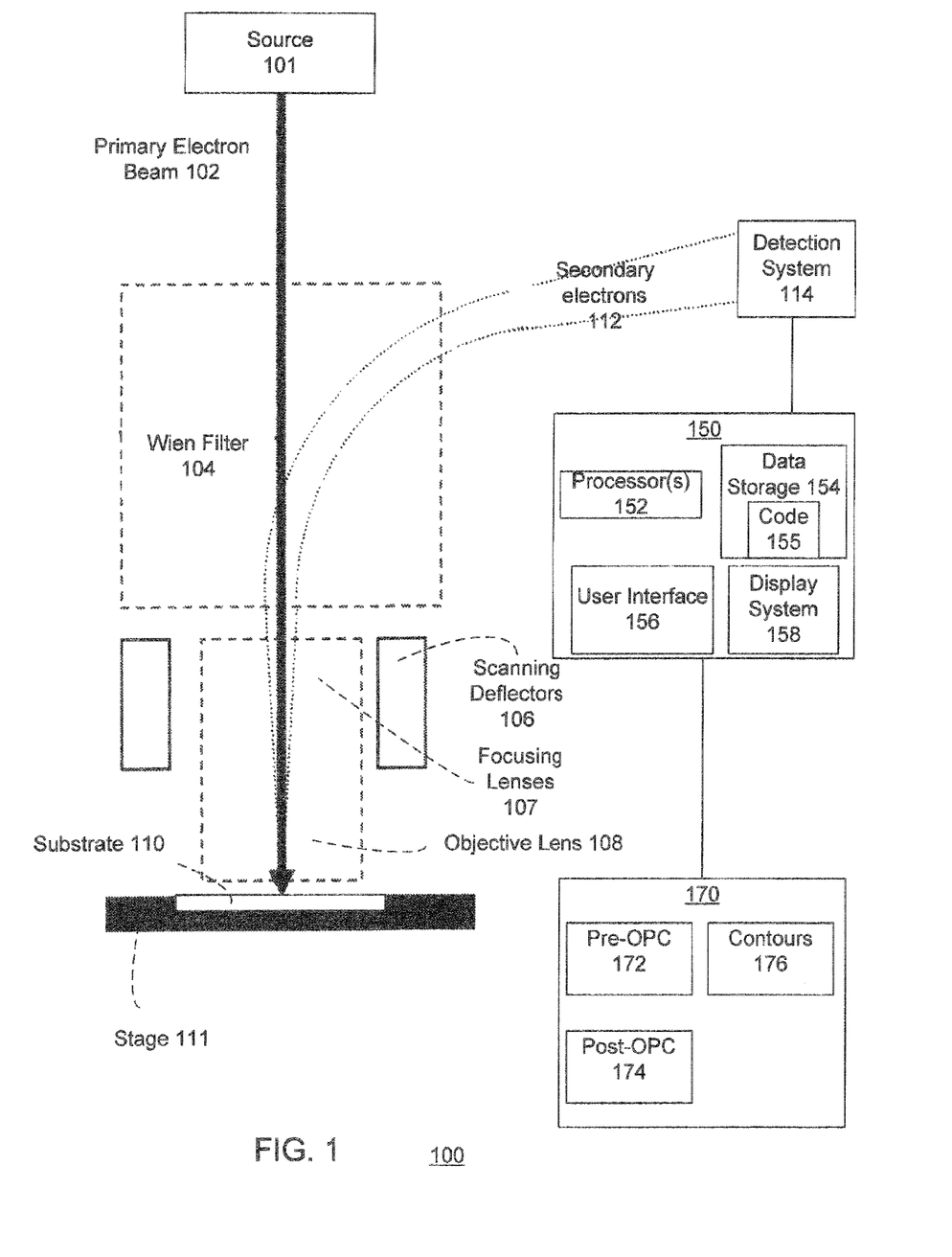
FIG. 1 is a schematic diagram of an e-beam apparatus in accordance with an embodiment of the invention.

FIG. 1 provides a cross-sectional diagram of the e-beam inspection apparatus 100 which may be utilized in accordance with an embodiment of the invention. As shown in FIG. 1, a source 101 generates an incident electron beam (primary electron beam) 102. The incident electron beam 102 passes through a Wien filter 104. The Wien filter 104 is an optical element configured to generate electrical and magnetic fields which cross each other. Scanning deflectors 106 and focusing electron lenses 107 are utilized. The scanning deflectors 106 are utilized to scan the e-beam across the surface of the target substrate 110. The target substrate 110 may be, for example, a patterned substrate, such as an integrated circuit being manufactured or a reticle for lithography.

The focusing electron lenses 107 are utilized to focus the incident electron beam 102 into a beam spot on the surface of the wafer or other substrate sample 110. In accordance with one embodiment, the focusing lenses 107 may operate by generating electric and/or magnetic fields.

As a result of the scanning of the incident electron beam 102, secondary electrons are emitted or scattered from the surface of the target substrate 110 (which may be, for example, a semiconductor wafer or a reticle). The target substrate 110 may be held by a movable stage 111. The secondary electrons are then extracted from the target substrate 110 by exposure to the electromagnetic field of the objective (final) lens 108. The electromagnetic field acts to confine the emitted electrons to within a relatively small distance from the incident electron beam optic axis and to accelerate these electrons up into the column. In this way, a secondary e-beam 112 is formed from the secondary electrons.

The Wien filter 104 deflects the secondary e-beam 112 from the optic axis of the incident electron beam 102 to a detection axis (the optic axis for the detection system 114 of the apparatus). This serves to separate the scattered e-beam 112 from the incident electron beam 102. The detection system 114 detects the secondary e-beam 112 and generates data signals that may be utilized to create images of the surface of the target substrate.

An instrument control and data processing (control/processing) system 150 may include one or more processors (i.e. microprocessors or microcontrollers) 152, data storage (including, for example, hard disk drive storage and memory chips) 154, a user interface 156 and a display system 158. The data storage 154 may be configured to store or hold computer-readable program code (instructions) 155 and data, and the processor 152 may be configured to execute the program code 155 and process the data. The user interface 156 may be configured to receive user inputs. The display system 158 may be configured to display views of the substrate surface to a user.

The control/processing system 150 may be connected to, and may be used to control, various components of the e-beam column so as to implement procedures disclosed herein. For example, the movement of the stage 111, and the scanning by the deflectors 106 may be controlled by computer-readable program code 155 executed by the control/processing system 150.

In addition, the control/processing system 150 may be configured to receive and process the electron image data from the detection system 114. In particular, the computer-readable program code 155 in the control/processing system 150 may be used to implement procedures relating to the contour-based defect detection technique which is described herein.

Furthermore, in accordance with an embodiment of the invention, the control/processing system 150 may be configured to interface with a design server 170. The design server 170 may be configured to store pre-OPC (optical proximity correction) design patterns 172, post-OPC design patterns 174, and image-extracted pattern contour data 176. During an inspection run, the design server 170 may provide said data in design clips in real time at the request of the control/processing system 150 of the e-beam inspection apparatus 100.

Figure 2:
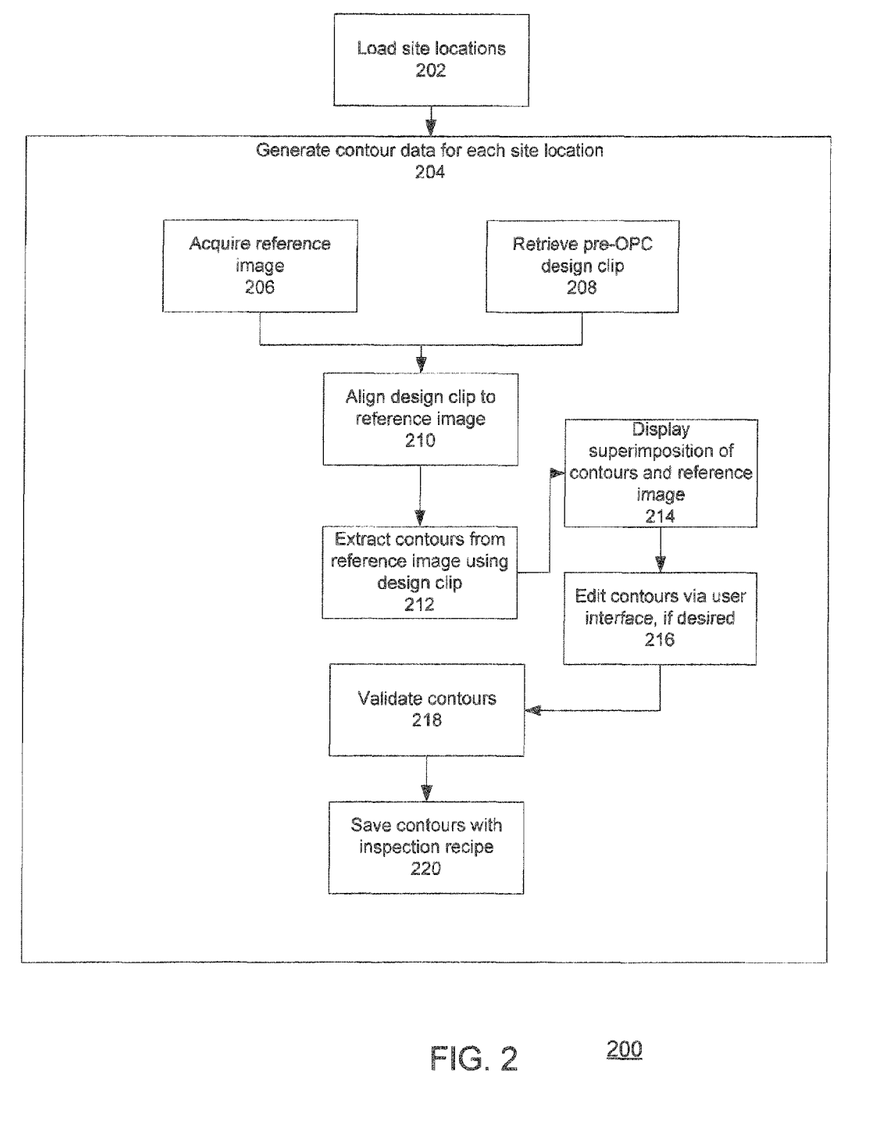
FIG. 2 is a flow diagram of a method for generating an image-extracted reference contour in accordance with an embodiment of the invention.

FIG. 2 is a flow chart of a method for generating an image-extracted reference contour in accordance with an embodiment of the invention. The method 200 may be performed using the e-beam inspection apparatus 100, for example, and may be performed as a preliminary method to set up.

Per block 202, the site location information (i.e. the locations of the sites to be inspected) may be loaded by the data processing system from a source. The site location information may be, for example, hots spots of a design rule check. Alternatively, the site location information may comprise inspection results from a previous inspection by the e-beam inspection apparatus 100 or by another inspection apparatus.

For each site location, a contour data generation procedure may be performed per block 204. As shown, the contour data generation procedure may involve performing the following steps (206 through 220) in order to generate and record the image-extracted reference contours and associated images for each site.

Per step 206, a reference image of a reference site may be loaded into a data processing system, such as the control/processing system 150, for example. The reference site is preferably a known good (defect free) site that corresponds to an inspection site. The reference image may be a SEM image that is acquired from the reference site by an imaging apparatus, such as the e-beam inspection apparatus 100, for example. The reference image is preferably acquired at a higher resolution than the resolution of the target images subsequently acquired during the inspection process.

Per step 208, a pre-OPC design clip may be retrieved for the site. The pre-OPC design clip may be retrieved from the design server 170 or from another source. The pre-OPC design clip provides a rendered image of the design pattern before the application of optical proximity correction. Per step 210, the design clip is aligned to the reference image.

Thereafter, per step 212, contours are extracted from the reference image. These contours are design-extracted reference-image contours and may be referred to herein as "reference contours". In accordance with an embodiment of the invention, the extraction of a reference contour using a design clip may be performed using a method 400 described further below in relation to FIG. 4.

At this point, per step 214, the reference contours may be displayed by superimposing them over the reference image, and the reference contours may be edited, if desired, via a user interface per step 216. After the reference contour has been extracted and optionally edited, the reference contours may be validated per step 218. The validation may be performed using additional reference images collected from another die on a wafer, for example.

Per step 220, the reference contours may then be saved or recorded in relation to an inspection (defect detection) recipe. The inspection recipe may be subsequently applied by the inspection apparatus 100 so as to inspect the site locations on a target substrate.

Figure 3:
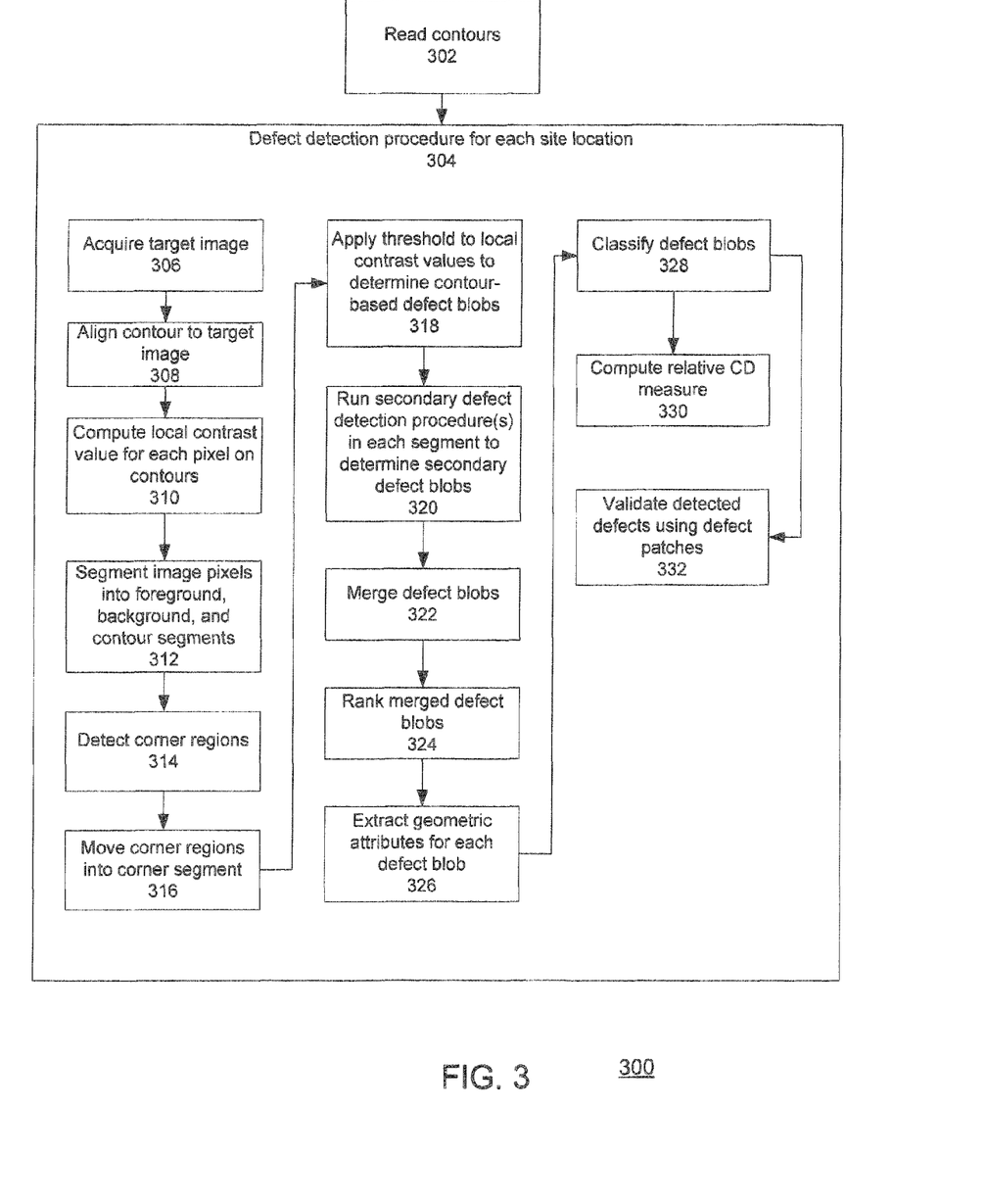
FIG. 3 is a flow diagram of a method for contour-based defect detection using an inspection apparatus in accordance with an embodiment of the invention.

FIG. 3 is a flow chart of a method 300 for contour-based defect detection using an inspection apparatus in accordance with an embodiment of the invention. The method 300 may be performed using the control/processing system 150 of the e-beam inspection apparatus 100, for example.

Per block 302, the reference contours may be read from storage for all inspection sites indicated by an inspection recipe. In one implementation, these reference contours and associated reference images may be loaded from data storage into memory of the control/processing system 150 of the e-beam inspection apparatus 100.

For each site location, a defect detection procedure may be performed per block 304. As shown, the defect detection procedure may involve performing the following steps (306 through 334) in order to detect and classify defects in a target substrate that is being inspected for defects.

Figure 5:
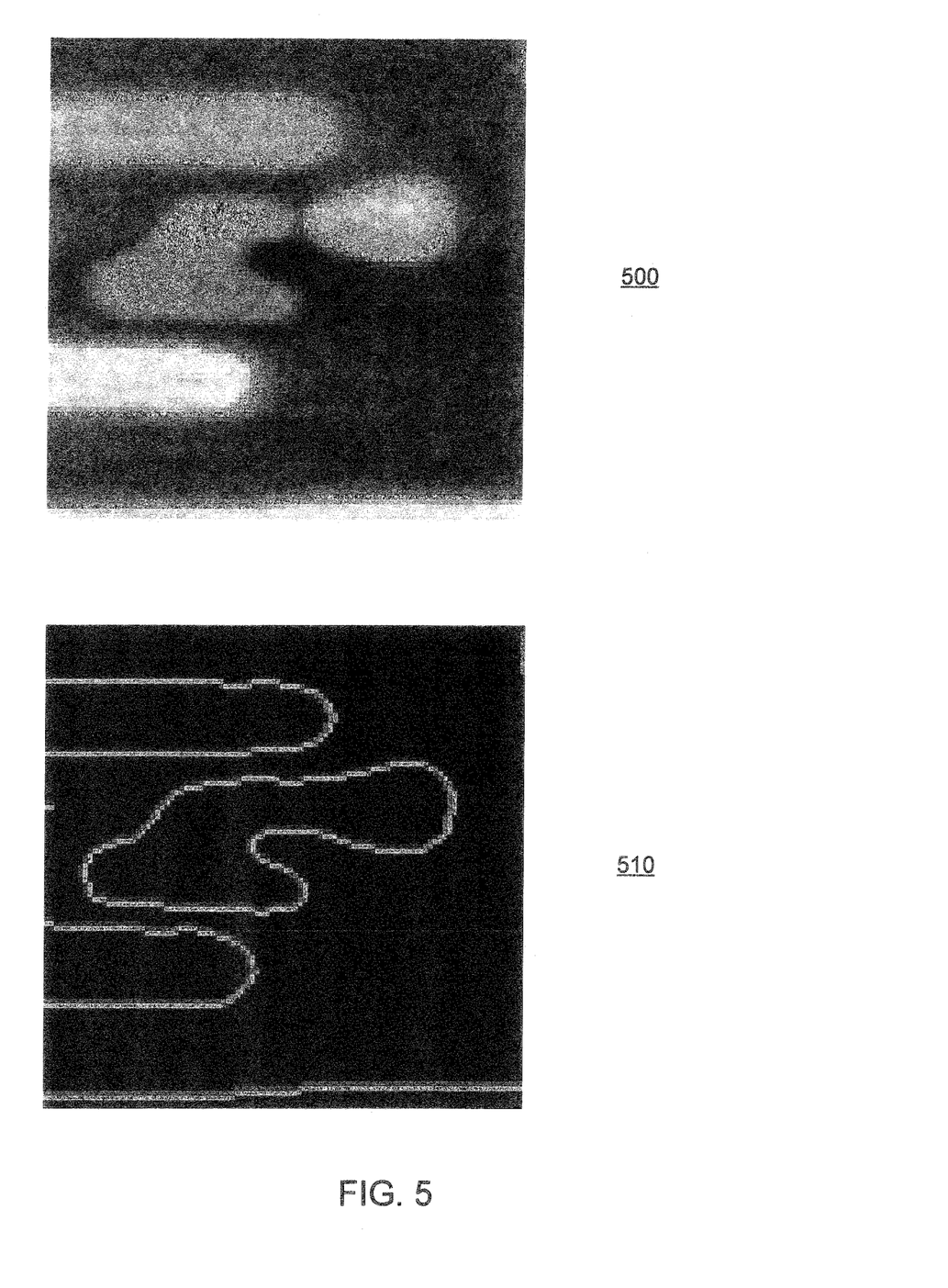
FIG. 5 shows an example of a target image and corresponding reference contours in accordance with an embodiment of the invention.

Per step 306, an image of an inspection site on the target substrate (i.e. a target image) may be collected or acquired. The target image may be a scanning electron microscope (SEM) image and may be collected using the e-beam inspection apparatus 100, for example. An example of a target image 500 and a corresponding reference contour 510 is shown in FIG. 5.

Per step 308, the reference contour for the inspection site may be aligned with the target image. In other words, the reference contour extracted previously from the reference site per the method 200 of FIG. 2 may be aligned to the target image of the corresponding inspection site on the target substrate.

Thereafter, per step 310, a local contrast value may be computed at each image pixel. The local contrast value for a pixel represents a difference (i.e. a contrast) between the value of the pixel in the target image and the value of the corresponding pixel from the image-extracted reference contour.

Per step 312, the image pixels may be segmented into foreground, background, and contour pixel segments based on the reference contour. The contour segment is made up of the pixels of the contours themselves. The procedure to distinguish foreground from background may start with seeds placed in the foreground based on the reference contour. Growing the regions from the seeds determines the foreground segment. The remaining pixels that are not part of the contour or foreground segments, may be determined to be the background segment.

In addition, corners may be detected using the curvature of the contours per step 314, and the corner regions (pixels in a local region surrounding the corner) may be removed from the previously-determined segments and put into a separate corner segment per step 316. For example, a bending of a contour of approximately ninety degrees may be determined to be a corner. Applicants have determined that placing the corner regions in a separate segment is advantageous because corners in a manufactured integrated circuit tend to have pattern variability.

Per step 318, automatic thresholding may be performed on the local contrast values for pixels in each image segment (foreground segment, background segment, contour segment and corner segment) to generate a contour-based defect pixel list per segment. The defect pixel list indicates the pixels in that segment which have local contrast above a threshold contrast value. Contour-based defect blobs (groups of adjacent defect pixels) may be determined from the contour-based defect pixel lists.

Per step 320, one or more secondary defect detection procedures may be run in each image segment (foreground segment, background segment, and corner segment). The secondary defect detection procedure(s) may utilize conventional die-to-die or cell-to-cell defect detection procedures, such as a segmented automatic threshold procedure or a multiple-die automatic threshold procedure. Each secondary defect detection procedure may generate a secondary defect pixel list for each segment. Secondary defect blobs may be determined from the secondary defect pixel lists.

Per step 322, the contour-based and the secondary defect blobs may be merged to create merged defect blobs. The merged defect blobs may be ranked per step 324. The ranking may depend, for example, on the local contrast and size of the defect blobs. To generate the ranking, an "energy" value may be computed which may be a sum of squares of the local contrast of the pixels of a defect blob. The ranking may then be done based on the energy values of the defect blobs.

Geometric attributes relating to each defect blob may then be extracted per step 326. The geometric attributes may be based on the location of the defect blob in relation to the contour pattern. For example, the geometric attribute may indicate the geometric shape (such as a square, or other polygon) in the contour pattern that the defect blob lies within. Other geometric attributes may be extracted.

The defect blobs may then be classified per step 328. In accordance with an embodiment of the invention, the defect classification may use the segment information and the geometric attributes of the defect blobs. In one embodiment, the segment information and geometric attributes may be used to classify the defect blobs into the following classes: short; open; bridging; necking; protrusion; intrusion; void; particle; and others.

Per step 330, a relative critical dimension (CD) measure may be computed. The relative CD measure may be computed by comparing the edges of the target image with the image-extracted reference contours.

For process window qualification, pattern fidelity metrics may be computed per step 332. Alternatively, for reticle requalification, the detected defects may be validated by using the defect pathes of a reticle inspection result per step 334.

Figure 4:
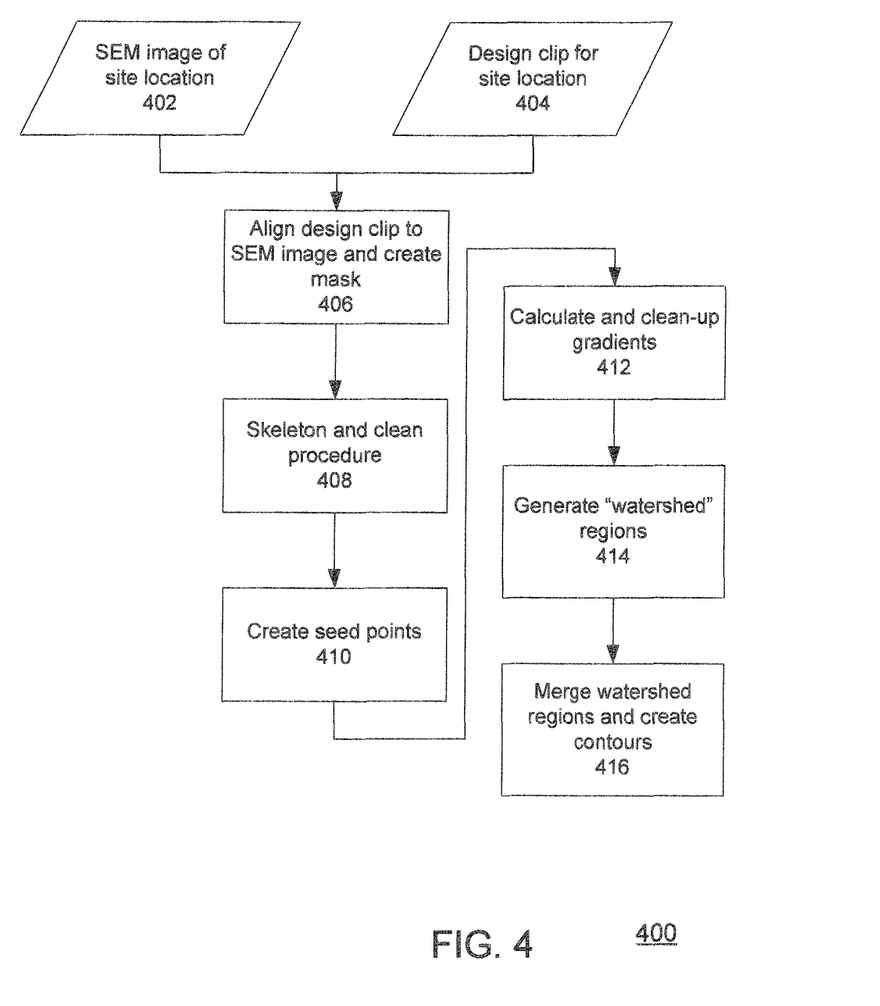
FIG. 4 is a flow diagram of a method of extracting a reference contour using a design clip in accordance with an embodiment of the invention.

FIG. 4 is a flow diagram of a method 400 of extracting a reference contour using a design clip in accordance with an embodiment of the invention. As shown, an SEM image 402 of the site location and a design clip 404 are input. Per step 406, the design clip may be aligned to the SEM image, and a mask for the SEM image may then be created from the aligned design clip.

A skeleton and clean procedure may be applied per step 408. This may involve obtaining an individual line segment for each individual region in the mask. The individual line segments may be separated at branch points so as to form the skeleton. The skeleton may be cleaned by removing line segments which are smaller than a pre-defined value.

Seed points may then be created per step 410. The seed point may be created by shrinking the remaining line segments into single seed points. A single region may have more than one seed point.

In addition, gradients may be obtained from the SEM image and cleaned-up per step 412. During the clean-up, gradients that lie within a dilated region of the masks may be retained so as to prevent leaks towards stronger gradients.

Per step 414, the seed points may be used to grow "minima" pools or "watershed" regions. Boundaries of each seed initiated pool or watershed region may be marked.

Finally, per step 416, the watershed regions may be merged, and final contours may be created based on the boundaries of the merged regions. The merging effectively fills holes that may be created by multiple seed points for a single region. The final contours may be given by "Sobel" edges.

FIG. 5 shows an example of a target image 510 and corresponding reference contours 520 in accordance with an embodiment of the invention. As seen, the reference contours 520 provide an expected outline for the regions of the target image 510.

Figure 6:
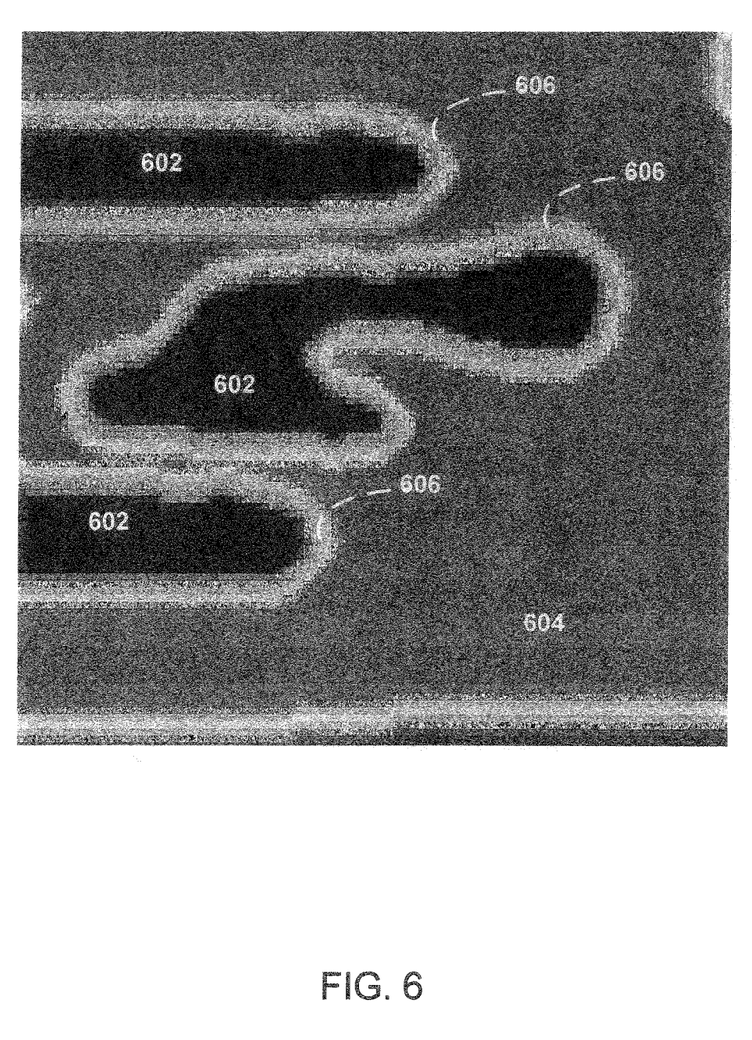
FIG. 6 shows the contours of FIG. 5 as segmented into foreground, background, and contour pixel segments in accordance with an embodiment of the invention.

FIG. 6 shows the contours of FIG. 5 as segmented into foreground 602, background 604, and edge (contour) 606 pixel segments in accordance with an embodiment of the invention. In this figure, the foreground segment 602 has the dark pixels, the edge segment 606 has the light pixels, and the background segment 604 has the medium-dark pixels.

Figure 7:
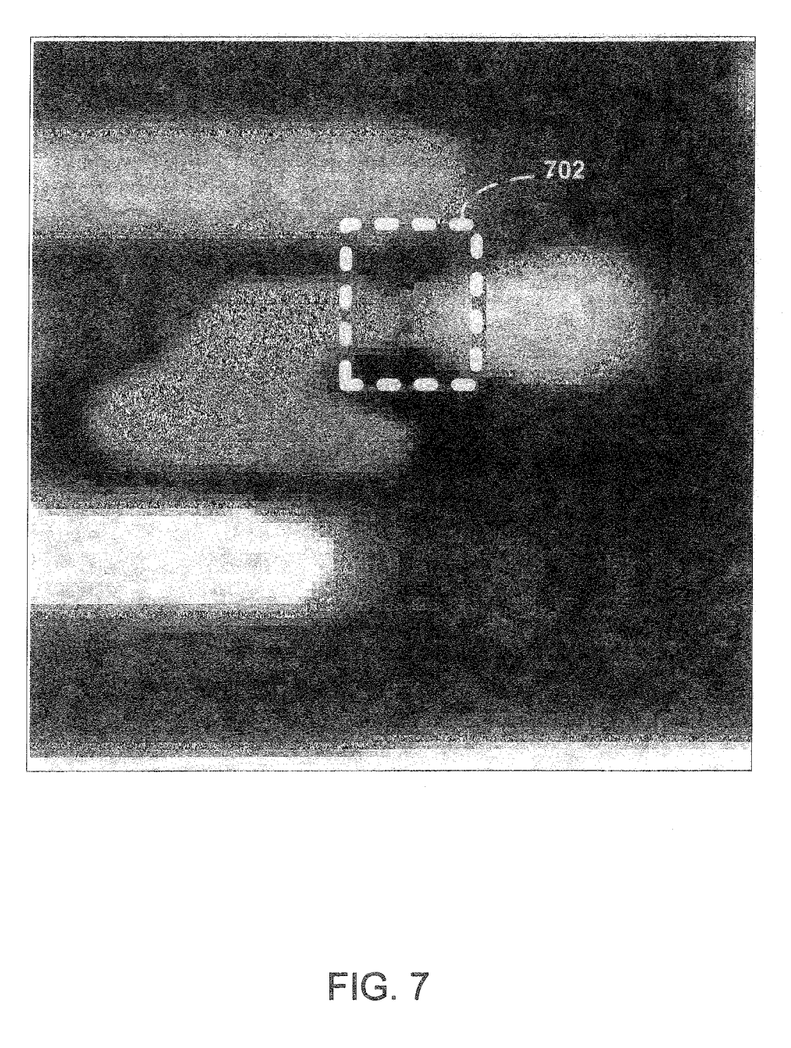
FIG. 7 shows a detected defect in the target image of FIG. 5 in accordance with an embodiment of the invention.

FIG. 7 shows a detected defect in the target image of FIG. 5 in accordance with an embodiment of the invention. As shown, the defect is within the rectangle 702 and appears to be a necking type defect.

Applicants have determined that defect detection using techniques described herein provides various advantages compared to conventional techniques. Compared to the conventional method of design rendering, the contour-based approach disclosed herein has substantially improved accuracy. Compared with the conventional die-to-die approach, the contour-based approach disclosed herein has substantially increased sensitivity.

These superior results are unexpected and counter-intuitive because the contour-based approach disclosed herein substantially neglects pixels interior to the contours. Despite this neglect of the interior pixels, superior results are provided by focusing on the contours themselves.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of inspecting a site location on a target substrate, the method comprising:
    obtaining contours which are generated from a reference image using a rendered image of a design pattern;
    acquiring a target image of the site location;
    aligning the contours to the target image;
    computing contrast values for pixels on the contours; and
    applying a threshold to the contrast values to determine contour-based defect blobs.

2. The method of claim 1, further comprising:
    segmenting the target image into at least a foreground segment, a background segment and a contour segment.

3. The method of claim 2, further comprising:
    distinguishing between foreground and background segments by a procedure which uses seeds placed in the foreground segment based on the contours.

4. The method of claim 2, further comprising:
    determining corner regions; and
    further segmenting the target region into a corner segment that includes pixels of the corner regions.

5. The method of claim 4, further comprising:
    executing a secondary defect detection procedure in each segment to determine secondary defect blobs.

6. The method of claim 5, further comprising:
    merging the contour-based defect blobs with the secondary defect blobs to obtain merged defect blobs;
    ranking the merged defect blobs; and
    classifying the merged defect blobs.

7. The method of claim 1, further comprising:
    generating the contours by acquiring the reference image of a reference site that corresponds to the site location;
    retrieving the rendered image of the design pattern of the site location;
    aligning the rendered image of the design pattern to the reference image; and
    extracting the contours from the reference image using the rendered image of the design pattern.

8. The method of claim 7, further comprising:
    validating the contours using additional reference images; and
    saving the contours with an inspection recipe.

9. A method of generating contours for use in inspecting a site location for defects, the method comprising:
    acquiring a reference image of a reference site that corresponds to the site location;
    retrieving a rendered image of a design pattern of the site location;
    aligning the rendered image of the design pattern to the reference image; and
    extracting the contours from the reference image using the rendered image of the design pattern.

10. The method of claim 9, further comprising:
    validating the contours using additional reference images; and
    saving the contours with an inspection recipe.

* * * * *